United States Patent [19]

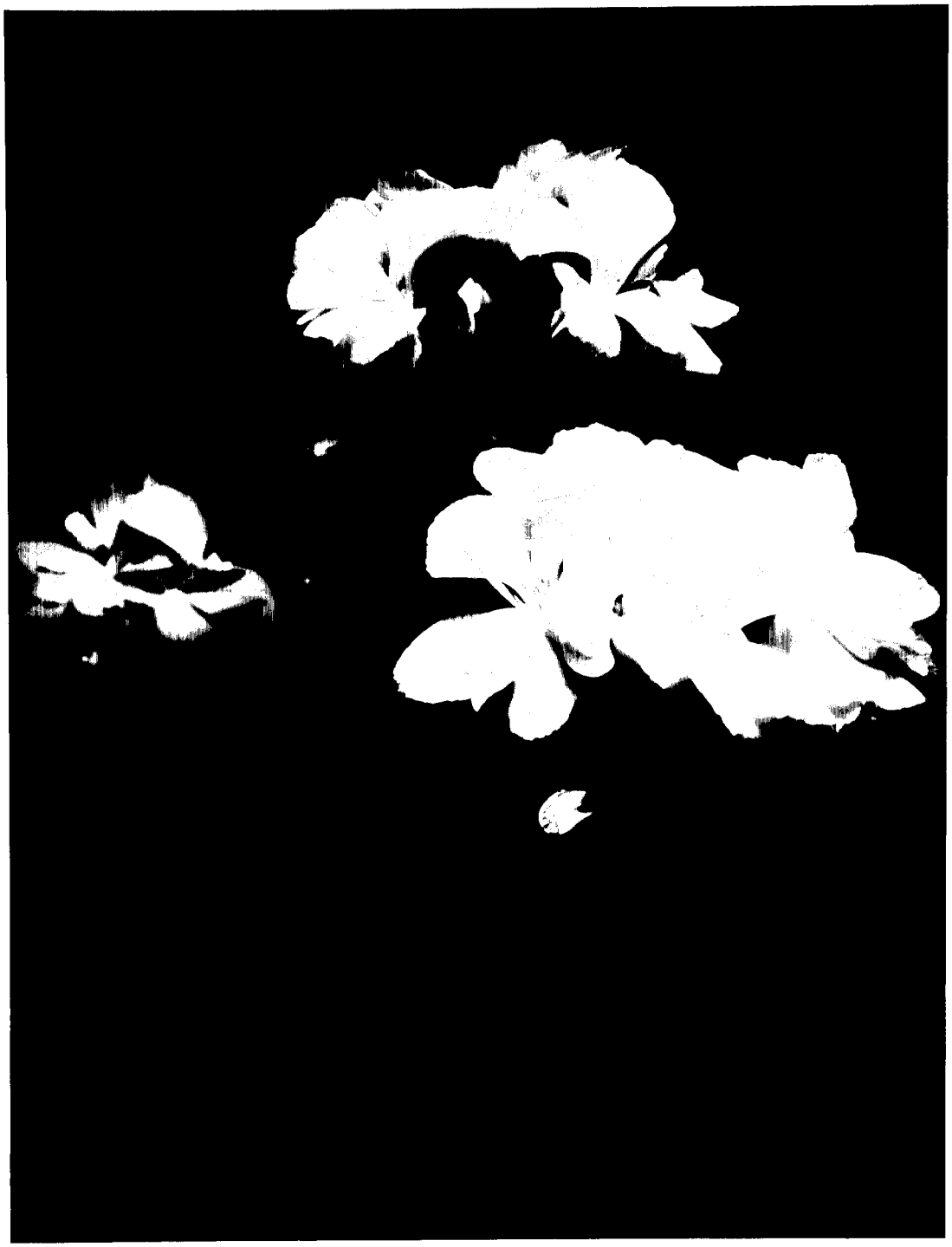

Buck

[11] Patent Number: Plant 5,759

[45] Date of Patent: Jul. 1, 1986

[54] GERANIUM PLANT NAMED LA SEVILLANA

[75] Inventor: Griffith J. Buck, Ames, Iowa

[73] Assignee: Iowa State University Research Foundation, Inc., Ames, Iowa

[21] Appl. No.: 673,104

[22] Filed: Nov. 19, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Tilton, Fallon, Lungmus

[57] ABSTRACT

A new variety of geranium plant distinguished by its profuse and vigorous flowering habit, its tolerance to foliar diseases in climates with high summer day and/or night temperatures and humidities, and the strong red color of its abundant flowers.

1 Drawing Figure

BACKGROUND OF THE NEW PLANT

This new variety originated as a seedling produced by crossing "Marian" (U.S. Plant Pat. No. 4,041) as the pollen parent with an unnamed variety in my stock resulting from crossing "Graffin Mariza" with "Galaxie" (both unpatented) as the seed parent. The cultivar was discovered by me at Iowa State University Horticulture Greenhouses, Ames, Iowa, in 1978 and resulted from breeding efforts begun by me in 1956 at that University. The breeding programme was undertaken in an effort to develop a cultivar having color and floral effects similar to those of older cultivars such as "Springtime" and "Summertime" (both unpatented) but having improved plant traits, particularly with respect to greater tolerance to higher temperatures and humidity and the ability to grow vigorously and flower profusely under such climatic conditions. Propagation of this new variety was carried out under my direction at Iowa State University, Ames, Iowa, by means of cuttings, and has been carried on through many generations which have clearly demonstrated that the distinctive characteristics of the plant hold true from generation to generation and are firmly fixed.

DESCRIPTION OF THE DRAWING

This new geranium plant is illustrated by the accompanying photographic drawing which shows blooms, buds, and foliage of the plant in full color, the colors shown as being closely true as can be reasonably obtained by conventional progressional photographic procedures.

DESCRIPTION OF THE NEW PLANT

The following is a detailed description of my new variety of geranium plant with the color designations according to The Royal Horticultural Society Colour Chart (R.H.S.C.C.).

THE PLANT

Origin: Seedling.

Parentage:

*Seed parent.*—An unnamed variety obtained by crossing "Graffin Mariza" with "Galaxie" (both unpatented).

*Pollen parent.*—"Marian" (U.S. Plant Pat. No. 4,041).

Classification:

*Botanic.*—*Pelargonium hybridum.*

*Commercial.*—Garden geranium.

Form: Bush.

Size: 35 to 45 cm. high and 35 to 45 cm. wide when grown outdoors (about 30 cm.×30 cm. as a four inch pot plant).

Growth: Vigorous, upright, and branching.

Strength: Sturdy with notable resistance to breaking apart when exposed to wind and rain.

Foliage: Abundant quantity.

*Leaves.*—Size: About 9 to 13 cm. long and 10 to 13 cm. wide. Shape: Rounded cordate with several rounded lobes with serrate margins. Texture: Leathery and slightly pubescent on both surfaces which feel hard to the touch. Color: Upper side: Dark Yellow-Green 146B (R.H.S.C.C.) with indistinct center zone of Lettuce Green 144A (R.H.S.C.C.). Under side: Scheele's Green 144B (R.H.S.C.C.). Ribs and veins: Not prominent on upper surface of leaf but conspicuous on under side.

Petioles: About 8.2 to 10.1 cm. in length.

THE BUD

Size: Large, having a diameter of about 1.2 to 1.5 cm. and a depth (length) of about 1.5 to 2.0 cm.

Shape: Pointed ovoid.

Opening: Bud opens slowly.

Color: When sepals first divide, and later when petals begin to unfurl, Crimson 52A (R.H.S.C.C.).

Sepals: Spear-shaped sepals that stand up and then curl back as the flower opens. Their outside and inside color is Scheele's Green 144B (R.H.S.C.C.) tinted with reddish brown.

THE FLOWER

Blooming habit: Continuous but indeterminate, blooming from early to late throughout the growing season and, with adequate temperature and photoperiod, flowering all year under glass.

Size: Very large, with a diameter of about 11.0 to 12.0 cm. and a depth of about 5.5 to 7.0 cm.

Borne: Inflorescence is an umbel.

Shape: Compact and approximately globular.

Florets:

*Form.*—Cup-shaped when bloom first opens, later flattening to a shallow cup-shape with maturity.

*Petals.*—7 to 8 in number; form is obovate, arrangement is imbricate, and texture is soft and satiny.

*Color.*—Both the outer and inner petals are Carmine Red 52B (R.H.S.C.C.) with whitish ground color at their bases. The reverse side of the petals are Carmine Rose 52C to 52D (R.H.S.C.C.). The petals darken with age.

Petaloids: 1 to 3 in number with sizes of approximately 1.5 cm. in length and 1.0 cm . in width. Their color is Carmine Red 52B (R.H.S.C.C.).

Persistence: The flowers hang on and dry with a lasting quality of about 7 days both on the plant and as cut flowers. The flowers are not appreciably affected by wet or hot weather.

Disease resistance: Plant is tolerant of foliar diseases common to geraniums, particularly *Botrytis cinerea.*

REPRODUCTIVE ORGANS

Stamens:

*Anthers.*—7 to 10 in number.

*Length.*—About 2.5 mm.

*Arrangement.*—Cylindrical.

*Filaments.*—About 5 to 7 mm. in length.

*Color.*—White tipped with Crimson Red 52A (R.H.S.C.C.).

*Pollen.*—Color — Red-brown.

Pistils:

*Number.*—One.

*Length.*—8 to 10 mm.

*Stigmas.*—Color — Crimson Red 52A (R.H.S.C.C).

Ovaries: 5-celled.

Fruit: Partially fertile.

*Shape.*—Ovoid with a long "beak".

*Color.*—Brownish-black at maturity.

This cultivar has flowers similar in color and floral effect to earlier varieties "Springtime" and "Summertime" but has improved plant traits more like those of "Galaxie," "Marian" (U.S. Plant Pat. No. 4,041), "Hazel" (U.S. Plant Pat. No. 4,040), and "Super Waltztime" (U.S. Plant Pat. No. 4,653) which were derived from the same breeding programme. Like these latter cultivars, this variety is tolerant of high temperatures and humidity and has the ability to grow vigorously and flower profusely under those climatic conditions. The flowering habit of this new variety is particularly profuse because of the shorter time period for the initiation of infloresences which are produced on a 1 to 3 node cycle.

I claim:

1. A new and distinct geranium variety substantially as herein shown and described, characterized by its abundant production of umbel-formed clusters of large florets, the uniform red coloring of its flowers, its tolerance of high day and night temperatures and humidity, and its ability to grow vigorously and flower profusely under those climatic conditions.

* * * * *